(12) United States Patent
Lee

(10) Patent No.: US 7,230,166 B2
(45) Date of Patent: Jun. 12, 2007

(54) VARIETY OF FOUR-LEAF CLOVER AND A METHOD FOR BREEDING THE SAME

(76) Inventor: Won-Kyung Lee, 1303-418 Sibeomdanjl, Apt., Seohyeon-dong, Bundang-gu, Seongnam-si, Gyeonggi-do (KR)

( * ) Notice: Subject to any disclaimer, the term of this patent is extended or adjusted under 35 U.S.C. 154(b) by 672 days.

(21) Appl. No.: 10/376,759

(22) Filed: Feb. 28, 2003

(65) Prior Publication Data

US 2003/0182693 A1 Sep. 25, 2003

(30) Foreign Application Priority Data

Feb. 28, 2002 (KR) .............................. 10-2002-0010912

(51) Int. Cl.
*A01H 5/00* (2006.01)

(52) U.S. Cl. ..................................................... 800/298
(58) Field of Classification Search .................. 800/298
See application file for complete search history.

(56) References Cited

FOREIGN PATENT DOCUMENTS

KR          100371928          1/2003

OTHER PUBLICATIONS

The New Royal Horticultural Society Dictionary of Gardening.*
http://www.lollysmith.com/lollysmith/allabsham.html.*
Lucky lore Theresa Hogue. Democrat–herald. Mar. 22, 2004.*

* cited by examiner

*Primary Examiner*—Andrew Wang
*Assistant Examiner*—Annette H Para
(74) *Attorney, Agent, or Firm*—McDonnell, Boehnen Hulbert & Berghoff

(57) ABSTRACT

Disclosed is a new variety of four-leaf clover named "Lucky Together", and a method of breeding the same in large quantities. The method of breeding the new variety of four-leaf clover of the present invention comprises the steps of: (a) sterilizing a clover, (b) treating the clover with chemical agent in order to induce mutation and cell division of the clover, (c) roots-inducing of the mutated clover, (d) asexual propagation of the variety of clover, (e) comparing the features of the variety with those of wild-type clover, and (f) identifying a uniformity of the features of the variety. The four-leaf clover according to the present invention has strong nature, strong cold resistance and excellent disease resistance. Furthermore, the clover according to the present invention grows rapidly and well under intensive light, and can compete successfully with weeds. Therefore, the clover can be used not only for feed but also for improving the quality of soil. Thus, the variety of clover has higher commercial and ornamental values.

3 Claims, 5 Drawing Sheets

VARIETY OF FOUR-LEAF CLOVER AND A METHOD FOR BREEDING THE SAME

PRIORITY CLAIM

This application claims the benefit under 35 U.S.C. § 119 of Korean patent application serial no. 10-2002-0010912, filed Feb. 28, 2002, granted as Korean Patent no. 10-0371982.

BACKGROUND OF THE INVENTION

1. Field of the Invention

The present invention relates to a variety of four-leaf clover and asexual propagation thereof.

2. Prior Art

There are more than 250 species of clovers. All are members of the pea family. The clovers are considered as being shamrocks, usually consisting of small round lobed leaves. The white clover (*Trifolium repense L.*) is actually native to the United States. It is a true perennial and has white flowers, and occasionally a four-leaf clover. Crimson clover (*Trifolium incarnatum*) is an annual clover commonly planted in the medians of the highway. It also has rounded lobed leaves with deep red blooms. In general, the clovers are classified into the white clover and the red clover (*Trifolium pratense L.*) according to the color of flower thereof. The white clover typically has a short and straight root, a small stem and three leaves. The white clover can be cultivated using a part of creeping stem, which also can be asexually propagated from root node. The white clover is classified as generally having white-color flowers. Each of the leaves of the white clover is egg-shaped, and is not aesthetic.

Floral languages of four-leaf clover are known as "the luck", "the hope", "the love" and "the faith", so that numerous people wish to keep the four-leaf clovers, but it is not easy to find the natural four-leaf clovers. Thus, since the four-leaf clovers have not only scarcity value but also ornamental value, they are considered as having great commercial values. Thereby, the four-leaf clovers have been used in the preparation of various articles, for example, an accessory, public relations goods, a present, a press flower and a dry flower, in order to attract consumers. Therefore, there have been needs to develop a new type of four-leaf clover, which grows rapidly and can be acclimated to environment easily.

The conventional clovers, which are native in Korea, are occasionally four-leaf clovers. Those clovers typically have oval shaped green leaves and relatively short stems, while having an excellent ground covering ability. Since the occasional four-leaf clovers are resulted from natural mutation, it is difficult to produce the four-leaf clovers massively.

On the other hand, a clover having three leaves, which was introduced from foreign countries into Korea and which has been cultivated and has been used as feed, includes a commercially available red clover class, for example, TR 2000, Titus, Kenland and Atlas. However, the clovers of those races are not only hard to cultivate but also are difficult to make them acclimated to the environment of Korea. Therefore, there have been needs to develop a new variety of four-leaf clover that grows well and has a strong nature.

SUMMARY OF THE INVENTION

The present invention has been developed to solve the above-mentioned problems.

It is an object of the present invention to provide a new variety of four-leaf clover.

It is another object of the present invention to provide a method of breeding the new variety of four-leaf clover.

In order to accomplish the first object of the present invention, there is provided a variety of four-leaf clover. In an aspect of the present invention, a part of stolon of a wild type clover is treated with a mutagen. More specifically, the part of stolon, which includes three leaves, is cut off from the white clover, and then is sterilized with ethyl alcohol. Next, the stem was treated again with mutase, such as EMS (Ethyl Methane Sulfonate), BAP (6-Benzylaminopurine), IAA (Indol-3-Acetic Acid) and NAA (α-Naphthaleneacetic Acid) in order to induce mutation, and incubated in a medium. Continuously, four-leaf clovers are selected from the shoots incubated in the medium, which are repeatedly cultivated. The variety of four-leaf clover is incubated in a medium to induce roots. The roots-induced clovers are transferred to a port, and appropriate stems are selected from the port. Then, tissue culture for the selected stems is carried out for five generations. Finally, features of the new variety of the four-leaf clovers are identified with comparison to the wild-type clovers, and the uniformity of the features of the variety is confirmed.

In order to achieve the second object of the present invention, there is provided a method of breeding the new variety of the four-leaf clover, in which the clover is propagated asexually. The method of breeding the new variety of the four-leaf clover of this invention comprises the steps of: a) sterilizing a clover, b) treating the clover with chemical agent in order to induce mutation and cell division thereof, c) root-inducing of the variety, d) asexual propagation of the variety of clover, e) comparing the features of the variety with the wild-type clover, and f) confirming uniformity of the features of variety.

In the step (a), a stolon segment including three leaves is cut off from a wild-type white clover, and all leaves are removed therefrom. Then, the segment, which contains growing point; is cut off again at a length of about 3 cm, which in turn is sterilized with ethyl alcohol. Finally, the sterilized segment is washed with distilled water.

In the step (b), the segment of the step (a) is treated with Ethyl Methane Sulfonate in order to induce mutation and vigorous cell division of the shoot segment of the white clover, which in turn is treated with 6-Benzylaminopurine, Indol3-Acetic Acid and α-Naphthaleneacetic Acid in a basic MS medium, also know to those skilled in the art as MS basal medium.

In the step (c), stems of a four-leaf clover, which is obtained by incubating the shoot segment of the white clover, is selected to induce roots in the medium.

In the step (d), the stem having roots is transplanted to a port so that a four-leaf clover may grow. Then, the stem of four-leaf clover is selected from the port and is subjected to tissue culture through 5 (five) generations; thereby a new type of four-leaf clover named "Lucky Together" is obtained.

In the step (e), the features of the variety of clover are investigated with comparison to those of the wild-type clover.

In the step (f), the stems and the roots of the variety of four-leaf clover are divided and transplanted, and then a uniformity of the variety is identified and established.

DESCRIPTION OF THE PREFERRED EMBODIMENTS

Figure 1:
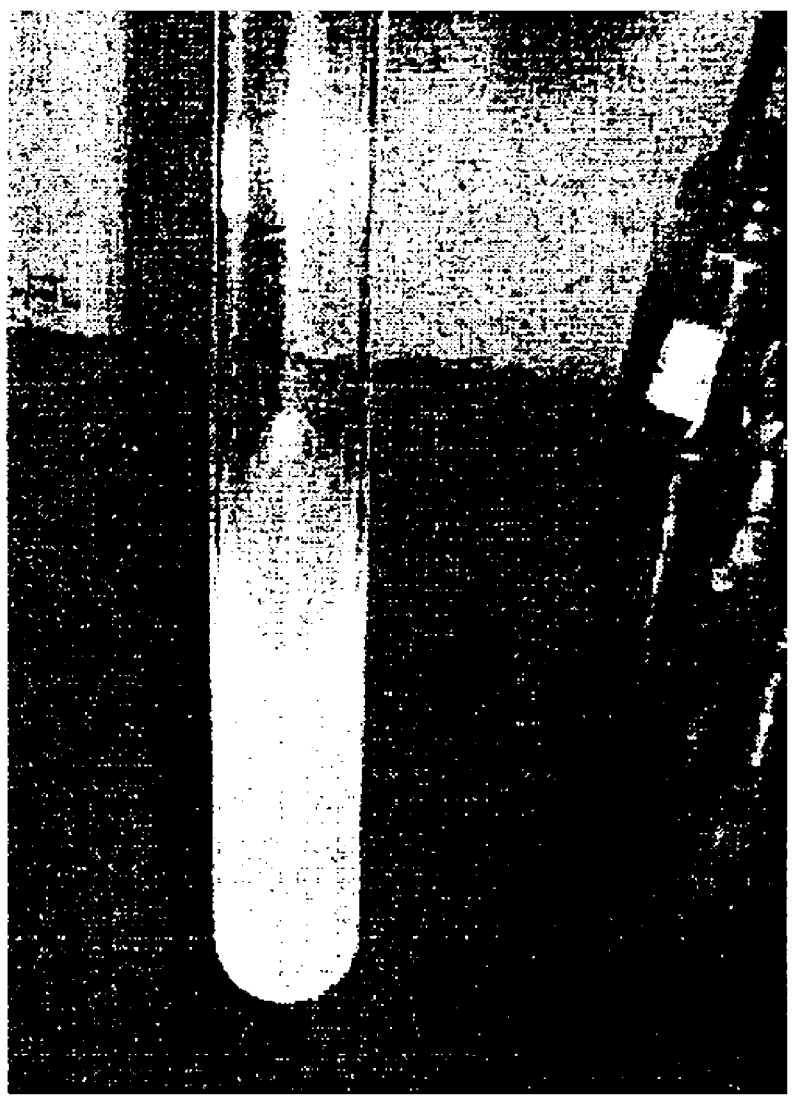
FIG. 1 is a photograph showing a MS basal medium of a new variety of a four leaflet clover according to the preferred embodiment of the present invention.

According to an aspect of the present invention, there is provided a method of breeding the new variety of the four-leaf clover. One of ordinary skill in the art would understand that the term "leaf" as used throughout this specification means the collection of leaflets that form a single "leaf" of a clover plant, as shown in FIG. 1.

The method of breeding the new variety of four-leaf clover of the present invention comprises the steps of: (a) sterilizing a clover, (b) treating the clover with chemical agent in order to induce mutation and cell division of the clover, (c) roots-inducing of the mutated clover, (d) asexual propagation of the variety of clover, (e) comparing the features of the variety with those of wild-type clover, and (f) identifying a uniformity of the features of the variety.

In the step (a), a stolon segment including three leaves is cut off from a wild-type white clover, and all leaves are removed therefrom. Then, the segment, which contains growing point, is cut off again at a length of about 3 cm, which in turn is sterilized with ethyl alcohol. Finally, the sterilized segment is washed with distilled water.

In the step (b), the segment of the step (a) is treated with Ethyl Methane Sulfonate in order to induce mutation and vigorous cell division of the shoot segment of the white clover, which in turn is treated with 6-Benzylaminopurine, Indol-3-Acetic Acid and α-Naphthaleneacetic Acid in a basic MS medium.

In the step (c), stems of a four-leaf clover, which is obtained by incubating the shoot segment of the white clover, is selected to induce roots in the medium.

In the step (d), the stem having roots is transplanted to a port so that a four-leaf clover can be raised. Then, the stem of four-leaf clover is selected from the port and is subjected to tissue culture through 5 (five) generations; thereby a new type of four-leaf clover named "Lucky Together" is obtained.

In the step (e), the features of the variety of clover are investigated with comparison to those of the wild-type clover.

In the step (f), the stems and the roots of the variety of four-leaf clover are divided and transplanted, and then a uniformity of the variety is identified.

More specifically, a stem including three leaves is cut off at a length of about 7 cm. The leaves are removed from the stem, and then the stem including the growing point is cut into several segments having a length of about 3~4 cm. Next, for sterilizing, the segments are transferred to and treated with a solution of ethyl alcohol of 70% for 30 seconds in a conical flask. Continuously, the segments of the stem are washed with sterile water three times. Then, the segments of the stem are cut off by a length of 2~3 mm in a clean bench, wherein each of the segments includes the growing point.

The cut segments are transferred to a solution of Ethyl Methane Sulfonate of about 0.1~0.3 μg/L for 3 seconds in the clean bench in order to induce mutation and cell division. Next, the cut segments are washed with sterile water. Then, the cut segments are incubated in a medium comprising the basic MS medium, 6-Benzylaminopurine of about 0.5~2.0 mg/L, Indol-3-Acetic Acid of 0.5 mg/L and α-Naphthaleneacetic Acid of 0.5 mg/L, thereby an individual organism of a four-leaf clover is generated. The above-processes are repeatedly carried out to produce a shoot of the four-leaf clover (See FIG. 1).

The segments of shoot are incubated in a medium to obtain the four-leaf clover. Then, a suitable stem is selected from the clover stems, which in turn is incubated in a medium comprising the basic MS medium, Indol-3-Acetic Acid of about 0.5~5.0 mg/L and α-Naphthaleneacetic Acid of about 0.5~5.0 mg/L. As the result, a shoot and a stem of the four-leaf clover are normally formed while fibrous roots are developed and grow in straight form.

The root-induced clover is transplanted to soil comprising a mixture of perlite, peat moss and sterilized sand in ratio of 1:1:1 under the conditions of humidity of 90%, temperature of about 18~20° C. and luminous intensity of 70% in a greenhouse. As the result, 90% of the stems are normally raised. A stem is selected from the four-leaf clover, which is obtained in the above-described manner, and is subjected to repetitive incubation through 5 generations. Then, the obtained clover is named "Lucky Together".

The features of clover, "Lucky Together", are investigated. When the features are compared with those of the wild-type clover, the clover of the present invention is a 5~10 cm longer than the wild-type clover, since the clover of this invention has nodes and grows above the ground separated from the ground surface while the wild-type has creeping stems.

Figure 2A:
FIGS. 2A and 2B are photographs showing the new variety of the clover having four leaflets according to the preferred embodiment of the present invention, in which shoots of the clover are respectively organized in different vessels.
Figure 2B:
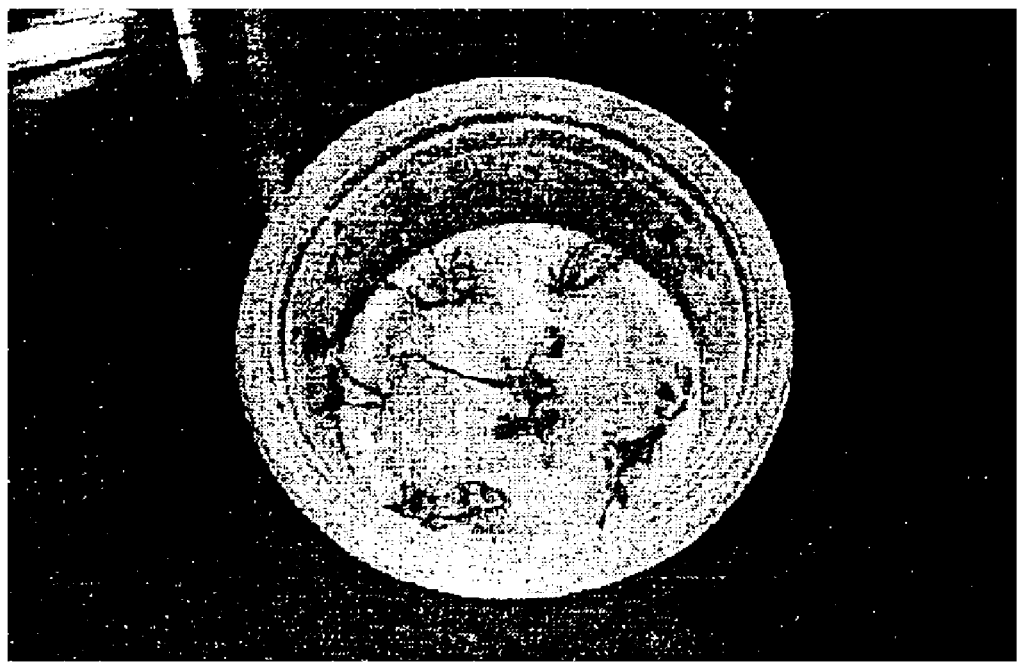

FIGS. 2a and 2b show the grown clover according to the present invention, which is transplanted to the vessels shown in the figures.

Figure 3:
FIG. 3 is a photograph showing the new variety of the four leaflet clover according to the preferred embodiment of the present invention, in which roots are induced in the test tube.
Figure 4:
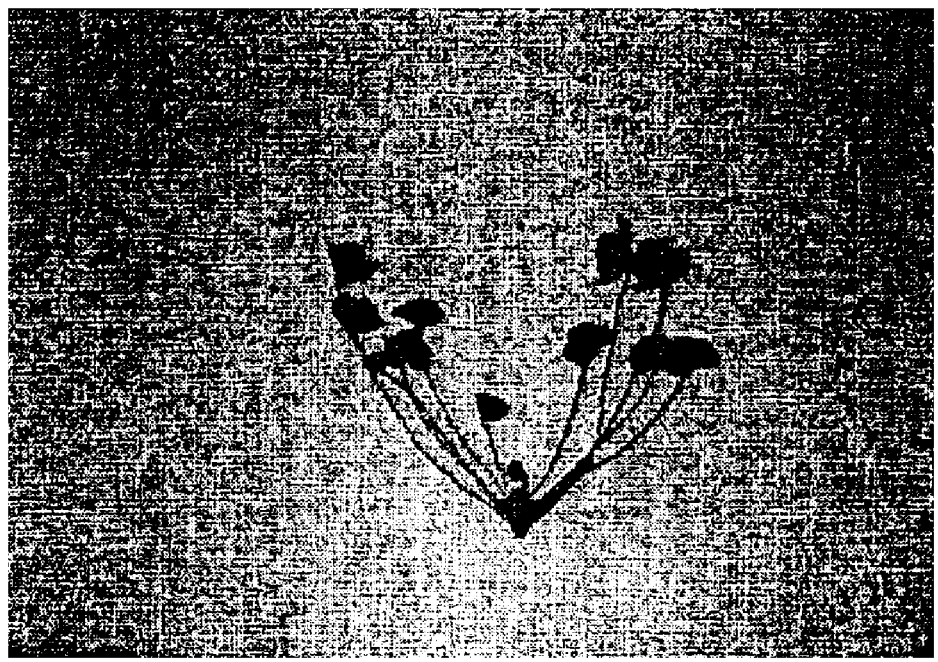
FIG. 4 is a photograph showing leaves and stems of the new variety of the clover having four leaflets according to the preferred embodiment of the present invention.

The new variety of the clover has four leaves which respectively has a heart shape, of which a respective length is shorter than that of the wild-type clover and of which a width is wide. In addition, the wild-type clover has leaves of dark green color, while the clover of the present invention has leaves of light green color (See FIG. 3). Meanwhile, FIG. 4 shows the clover according to the present invention, in which the leaves of the clover have a heart shape.

The four leaves are generated from one stem, and three white flowers achieve raceme. The wild-type clover is typically cultivated for 2 or 3 years, while the clover, "Lucky Together", can be annually cultivated.

The clover of the present invention has a strong nature and an excellent growth potential. The clover can be cultivated even under a strong light, and has strong resistance against cold and disease. Furthermore, the present clover can successfully compete with weeds. Furthermore, since the present clover has the roots extending straight under the ground and has higher growth rate, it can be cultivated fairly easily in a sterile land. Thus, the clover can be used to improve soil quality. In addition, it is suitable to utilize the clover as feed for domestic animals, since a harvest quantity of the clover is high.

As described above, the new variety of the clover is divided or cut into several roots cut and transplanted in greenhouse. These procedures are numerously repeated while individuals are continuously selected, which have excellent features of, for example, shape and color of a leaf, ground surface coverage rate, growing conditions such as temperature, humidity, luminous intensity and the like, and propagation manner. Also, these clovers must have such excellent features as a commercial value, a ornamental value, adaptability to environment, nutrition and growth conditions, disease resistance and the like. The new variety of the clover according to the present invention, "Lucky Together", is obtained in such a manner that the clover having the above-described features is selected. Finally, its character, its uniformity, and its stability were identified.

Hereinafter, the method of asexual propagation of the clover according to the present invention will be described in detail, but it is understood by those skilled in the art that the scope of the present invention should not be limited to this embodiment of the present invention.

Breeding a new variety of a clover, "Lucky Together"

Two hundreds of wild-type white clovers, which were native in Korea, were harvested, wherein the respective clovers had three leaves and a stem of a length of about 7 cm.

All leaves were removed from the clovers. Then, the stems of the clovers were cut at a length of about 3~4 cm, which are transferred to a conical flask and subjected to a solution of ethyl alcohol of 70% for 30 seconds to sterilize the stems. Next, the segments of stems were washed with sterile water, which in turn were transferred to a solution of ethyl alcohol of 70% for 15 minutes to sterilize surfaces of the stem segments. Continuously, the stem segments were washed with sterile water three times.

The sterilized segments of the white clovers were cut again at a length of 2~3 mm in a clean bench, wherein each of the cut segments included growing point. The resulting cut segments of the white clover were treated with Ethyl Methane Sulfonate in order to induce mutation. The result is shown in Table 1.

Referring to the Table 1, shoots were respectively treated with Ethyl Methane Sulfonate of 0.1~0.3 µg/L for 3 seconds. As the result, when the shoots were treated with Ethyl Methane Sulfonate of 0.2 µg/L, the ratio, regarding the growth of four leaves from the stem, is highest.

Furthermore, in order to promote mutation and cell division of shoots of the white clover, the shoots were treated with cold water of 5° C. for 20 seconds, which in turn were transferred to a solution of Ethyl Methane Sulfonate of 0.2 µg/L for 3 seconds. Then, the shoots were washed with sterile water. Subsequently, the shoots were incubated in a medium comprising a basic MS medium, 6-Benzylaminopurine of 1.5 mg/L, Indol-3-Acetic Acid and α-Naphthalene Acetic Acid of 0.5 mg/L. The effects of the mutagen on the shoot cultivation are shown in Table 2. The incubation of the shoots was carried out under the conditions of temperature of 21° C. and luminous intensity of 500 lux.

TABLE 1

Effects of Ethyl Methane Sulfonate on the mutation of the shoots

| Mutagen (µg/L) EMS | Time (sec.) | Mutation ratio (%) | Features of mutated clover | | | | |
|---|---|---|---|---|---|---|---|
| | | | Heliophilous | Numbers of stems | Numbers of leaves | Shape of leaves | Color of leaves |
| Control | 3.0a | 30a | 2.8c | 12a | 4a | — | |
| 0.1 µg/L | 3.0a | 12c | 0.3c | 6c | 4c | Heart | Light green |
| 0.2 µg/L | 3.0a | 25a | 1.5a | 10b | 4a | Heart | Light green |
| 0.3 µg/L | 3.0a | 18b | 2.5b | 8b | 4b | Heart | Light green |

Notes:
[a]Duncan's multipe range test (P ≦0.05)
[b]– none, ++ medium, +++ excellent

TABLE 2

Effects of a mixture of 6-Benzlaminopurine, Indol-3-Acetic Acid and α-Naphthalene Acetic Acid on the shoot propagation of the clover

| Treatment (mg/L) | Numbers of shoots/ segments | Length of shoots (cm) | Weight of shoots/ segments (g) | Callus formation | transparency ratio (%) |
|---|---|---|---|---|---|
| Control | 1.2 c[a] | 5.7 a | 3.42 a | –[b] | 10.1 b |
| BAP 0.5 + IAA 0.5 | 1.8 bc | 3.6 bc | 2.67 b | ++ | 39.4 a |
| NAA 0.5 | 1.2 c | 3.1 c | 2.22 b | –+ | 40.6 a |
| BAP 1.0 + IAA 0.5 | 2.7 ab | 4.1 b | 2.18 b | +++ | 46.2 a |
| NAA 0.5 | 2.4 b | 3.9 b | 2.43 b | +++ | 49.1 a |
| BAP 2.0 + IAA 0.5 | 3.3 a | 4.2 b | 2.52 b | +++ | 42.3 a |
| NAA 0.5 | 2.6 b | 4.0 b | 2.14 b | +++ | 52.6 a |

Notes: [a]Duncan's multiple range test (P ≦ 0.05)
[b]– none, ++ medium, +++ excellent
Medium: basic MS medium
Proliferation of shoots: MS + BAP 0.5 + IAP 0.5 + NAA 0.5 + SUCROSE 10~30 g/L
Proliferation of roots: MS + BAP 0.5 + IAP 0.5 + NAA 0.5~50 + SUCROSE 20 g/L Meanwhile, sucrose of 10~30 mg/L was added to the medium in order to reduce the callus formation and the transparency ratio during the cultivation of the shoots. The effects of the sucrose density on the propagation and the shoot growth are shown in Table 3.

TABLE 3

Effects of the density of sucrose in the medium on the propagation and the growth of shoots of the clover

| Sucrose (mg/L) | Numbers of shoots/ segments | Length of shoots (cm) | Weight of shoots/ segments (g) | Callus formation | transparency ratio (%) |
|---|---|---|---|---|---|
| 10 | 3.2 a[a] | 3.2 a | 1.66 a | +[b] | 3.46 b |
| 15 | 3.9 a | 4.1 a | 2.13 ab | + | 40.1 a |
| 20 | 4.0 a | 4.8 a | 2.17 ab | + | 46.7 a |
| 25 | 3.6 a | 3.9 a | 2.43 ab | ++ | 42.4 a |
| 30 | 3.4 a | 4.4 a | 2.73 a | +++ | 50.7 a |

Notes: [a]Duncan's multiple range test (P ≦ 0.05)
[b]– bad, ++ medium, +++ excellent
Medium: basic MS medium + BAP 2.0 mg/L + IAA 0.5 mg/L A culture vessel (control sample) and a milipore vessel, on which a milipore band (3 M) was attached in twofold in order for air to pass through the milipore band, were used to reduce the transparency ratio of the shoots in the medium. Then, the effects of ventilation in the culture vessel relating to the callus formation and the transparency ratio of the shoots were investigated. The result is shown in Table 4.

TABLE 4

Effects on the callus formation and the transparency ratio of the ventilation in the culture vessel

| Treatment | Numbers of shoots/ segments | Length of shoots (cm) | Weight of shoots/ segments (g) | Callus formation | transparency ratio (%) |
|---|---|---|---|---|---|
| Control | 3.4 a[a] | 4.1 a | 2.64 a | +[b] | 4.03 |

TABLE 4-continued

Effects on the callus formation and the transparency ratio of the ventilation in the culture vessel

| Treatment | Numbers of shoots/ segments | Length of shoots (cm) | Weight of shoots/ segments (g) | Callus formation | trans-parency ratio (%) |
|---|---|---|---|---|---|
| Milipore vessel c | 3.2 a | 3.6 a | 2.21 b | – | — |

Notes: [a]Duncan's multipe range test (P ≦ 0.05)
[b]– none, + bad
[c]Diameter: 1 cm, Milipore band (3M): double attachment
Medium: basic MS medium + BAP 2.0 mg/L + IAA 0.5 mg/L + SUCROSE 20 g/L In addition, the shoots were cultivated in the medium comprising the basic MS medium, Indol-3-Acetic Acid of 0.5~5.0 mg/L and α-Naphthalene Acetic Acid of 05~5.0 mg/L. Effects of the medium on the growth of roots of the cultivated shoots were investigated. The cultivation was carried out under the conditions of acidity of pH 5.5, 22~25° C. and luminous intensity of 800 lux. The results of examination are shown in Table 5.

TABLE 5

Effects of IAA and NAA on the shoot growth of the clover.

| Sucrose (g/L) | Numbers of shoots/ segments | Length of shoots (cm) | Numbers of roots/ segments | Length of roots (cm) | Weight of shoots/ segments (g) |
|---|---|---|---|---|---|
| Control | 1.2 c[a] | 4.6 a | 1.6 b | 5.4 a | 3.36 b |
| IBA 0.5 | 1.4 a | 5.1 a | 2.2 ab | 4.9 a | 3.4 ab |
| IBA 1.5 | 1.2 a | 5.3 a | 2.8 ab | 4.6 a | 4.66 a |
| IBA 2.0 | 1.0 a | 5.1 a | 3.4 a | 5.1 a | 4.21 a |
| IBA 5.0 | 1.0 s | 4.7 a | 1.2 b | 3.1 b | 3.33 b |
| NAA 0.5 | 1.0 a | 4.6 a | 3.2 a | 4.8 a | 3.92 a |
| NAA 1.0 | 1.1 a | 4.8 a | 2.5 ab | 3.6 ab | 4.21 a |
| NAA 2.0 | 1.2 a | 4.8 a | 1.9 b | 3.4 a | 3.42 ab |
| NAA 5.0 | 1.0 a | 4.2 a | 1.6 b | 3.2 b | 3.72 ab |

Notes: [a]Duncan's multipe range test (P ≦ 0.05)
Medium: basic MS medium + SUCROSE 20 g/L In the examination according to the present invention, the incubation efficiency of the shoots was enhanced in proportion to the density of the BAP. The average number of the shoots was more than 2.7 in the medium to which BAP of 1.0~2.0 mg/L was added. However, the callus, generated from each base of the shoots, inhibited the shoot growth. Thereby, the transparency ratio was more than 42.3%. See the Table 2.

Also, the sucrose density was adjusted in the medium in order to decrease the callus formation. As the result, it was observed that the callus was generated only in the medium to which the sucrose of 15~20 g/L was added. See the Table 3.

Furthermore, the shoots were cultivated in the milipore vessel to reduce the transparency ratio of shoots. As the result, the transparency of shoots was not observed at all. See the Table 4.

The rooting of the shoots was induced well in the medium in which IBA of 0.5 mg/L or NAA of 0.5~1.0 mg/L was added to the basic MS medium. See the Table 5.

Asexual propagation of the new variety of clover

Once the shoots and roots of the clover according to the present invention were generated in the medium as described above, the shoots were moved to a greenhouse under the environment of the humidity of 90%, the temperature of 18~20° C. and the luminous intensity of 70%, which in turn were transplanted to soil in which perlite, peat moss and sterilized sand were mixed with each other in ratio of 1:1:1. Then, water (about 18° C.) was supplied to the shoots at 9~10 AM and 4~5 PM everyday. As the result, the shoots of 90% were normally raised. The stems of four-leaf clover are obtained in such a way as described above, and were asexually propagated by tissue culture through 5 generations.

The results of comparing the method of tissue culture with the method of cuttage reproduction are shown in Table 6. In the asexual propagation, many of the four-leaf clovers are represented. From the four-leaf clovers, individuals that have excellent features of, for example, shape and color of a leaf, ground coverage rate, growth conditions such as temperature, humidity and luminous intensity, and the propagation manner, were selected. Also, the clovers were selected according to their commercial and ornamental value, adaptability to the environment, the nutrition and growth conditions and the disease resistance. Then the uniformity of features was identified and established. And, the established four-leaf clover was named "Lucky Together".

TABLE 6

Comparison between the tissue culture and cuttage

| | Plant issue culture | Cuttage |
|---|---|---|
| Numbers of individuals | 7 shoots/node | 1 shoot/node |
| Time-period of reproduction | All year around | Early spring, or autumn |
| Time required for reproduction | 6 weeks | One year |
| Place | Test tube | Wide area |
| Payroll cost | A person | Many person |
| Numbers of individuals/a year | 1000 plants | 40~50 plants |

Investigation of the features of the clover according to the present invention

The features of the variety of clover according to the present invention were investigated and compared with those of the wile-type clover that has generally three leaves. The results of comparison are shown in Table 7.

TABLE 7

Comparison of the features of the clover of the present invention with the wild-type clover.

| Features | New variety of clover | Wild-type clover |
|---|---|---|
| Height | 7~25 cm | 5~20 cm |
| Numbers of leaves | Four | Three |
| Shape of leaves | Heart | Ellipse |
| Surface of leaf | Fluffy | Lusterless |
| Periphery of leaf | A pattern of teeth of comb | A pattern of teeth of comb |
| Length of leaf | 0.3~2.5 cm | 0.7~3.0 cm |
| Width of leaf | 0.3~2.5 cm | 0.5~2.0 cm |
| Color of leaf | Light green | Dark green |
| Shape of stem | Separated from ground surface | Creeping on ground |
| Numbers of stems | 6~10 stems | Irregular |
| Shape of roots | Straight | Creeping or straight |
| Lifetime | Annual | Perennial |
| Flowering time | June | June |
| Shape of flower | Raceme having three receptacles | Raceme |
| Color of flower | White | White or pink |
| Heliophilous | Less heliophilous | heliophilous |

TABLE 7-continued

Comparison of the features of the clover of the present invention with the wild-type clover.

| Features | New variety of clover | Wild-type clover |
| --- | --- | --- |
| Disease endurance | Strong | Strong |
| Cold resistance | Strong | Strong |
| Growth rate | Rapid | Rapid |
| ornamental value | Valuable (light green, four-leaf) | Worthless (oval shape) |

As disclosed in the table 7, the clover of the present invention has four leaves. Each of leaves has a wide heart shape and a shorter length than the wild-type clover. The length of clover of this invention is about 5–10 cm longer than that of the wild-type, since the solon of the clover of this invention grows separated from the ground surface unlike the wild-type. Furthermore, the clover according to the present invention is light green in color, while the wild-type clover is dark green.

The leaves and the stems of clover of the present invention are shown in FIG. 4. Referring to FIG. 4, four leaves extended from one node of the clover, and the flower is a raceme having three white receptacles. The clover according to the present invention, "Lucky Together", is an annual plant, while the wild-type clover is a perennial plant.

The new variety of the clover of this invention has strong nature, excellent cold and disease resistance. The clover is able to be cultivated under intensive light. Also, since the roots extend straight through underground, the clover can propagate more rapidly and grow well in sterile soil. Furthermore, harvest amount of the clover is much greter than that of the wild-type clover. Therefore, the clover according to the present invention can be used for feed and for the improvement of the soil quality.

Comparison between plant tissue culture and cuttage propagation of the "Lucky Together".

Asexual propagation methods were compared in this study.

Propagation of the clover according to the conventional cuttage required relatively wide space and much time. In addition, seed dormancy and limited seed numbers were restrictive factors to the propagation by the method. Whereas, tissue culture of the clover brought out virus free plants and rapid propagation all year round, thereby it could save great deal of time and land spaces.

The asexual propagation of tissue culture and vegetative propagation, such as cuttage and layerage, generated the four-leaf clover having the same characters as those of the parent. Furthermore, since the breed of the clover was established, sexual propagation like sowing of seeds was possible.

As described above, leaves and stems are firstly selected from the wild-type clover having three leaves, and are treated with Ethyl Methane Sulfonate, 6-Benzylaminopurine, Indol-3-Acetic Acid and α-Naphthalene Acetic Acid in order to induce mutation. Then, repetitive tissue culture was carried out with the selected and mutated stems. Thereby, the four-leaf clover was generated, wherein the clover had strong nature, strong cold resistance, excellent disease resistance, and high commercial and ornamental values. Furthermore, the clover according to the present invention grows rapidly under intensive light. Furthermore, it can successfully compete even with weeds. Therefore, the clover according to the present invention can be used in horticulture industry, constructing grassland, improving the quality of soil and providing feed for domestic animals.

While the present invention has been particularly shown and described with reference to particular embodiments thereof, it will be understood by those skilled in the art that various changes in form and detail may be effected therein without departing from the spirit and scope of the invention as defined by the appended claims.

What is claimed is:

1. A method of breeding a new variety of four leaflet clover from a wild-type three-leaflet clover, Trifolium repens L., the method comprising the steps of:

(A) providing stem segments containing leaves of the wild-type three leaflet clover, which includes the sub-steps of:
   (a) cutting each of the leaved stems of the wild-type three-leaflet clover at a length of about 5 cm;
   (b) removing the leaves from the stem and cutting each of the stems including a growing point at a length of 3–4 cm;
   (c) transferring the segments into a conical flask and treating them with a solution of ethyl alcohol of 70% for 20 to 30 seconds to sterilize the segments and washing the segments with sterile water three times;
   (d) treating the segments with a solution of NaOCl of 1.0% for 15 minutes to sterilize the segments and washing the segments with sterile water three times;

(B) cutting each of the sterilized segments from step (A)(d) at a length of 2–3 mm in a clean bench, wherein each of the cut segments includes a growing point allowing shoots to grow from the segments;

(C) treating the shoots obtained from step (B) with cold water at a temperature of 5° C. for 20 seconds; treating the shoots with Ethyl Methane Sulfonate of 0.1–0.3 μg/L for 3 seconds; washing the shoots with sterilized water; and then incubating the sterilized shoots in a MS basal medium supplemented with 6 Benzylaminopurine of 0.5–2.0 mg/L, Indol-3-Acetic Acid of 0.5 mg/L and α-Naphthalene Acetic Acid of 0.5 mg/L under 500 lux illumination at 20–22° C.; and (D) obtaining a new variety of four-leaflet clover from the shoots obtained from step (C), including the sub-steps of:
   (a) transplanting the shoots to soil comprising a 1:1:1 mixture of perlite, peat moss and sterile sand in a greenhouse under the environment of humidity of 90%, temperature of 18–20° C. and illumination intensity of 70%, when a bud and roots are generated in the supplemented MS basal medium;
   (b) selecting shoots of the four-leaflet clover obtained from step (D)(a) and propagating the shoots asexually by repeated tissue-culture of the segments throughout 5 generations; and
   (c) subjecting the stems and roots of the four-leaflet clover to dividing/transplanting or cuttage to obtain a new variety of four-leaflet clover.

2. The method as claimed in claim 1, wherein at the step (C) the concentration of 6-Benzylaminopurine is about 1.0–2.0 mg/L and sucrose with a concentration of about 15–20 g/L is further added to the MS basal medium, thereby reducing callus formation and the transparency ratio.

3. A new variety of four-leaflet clover bred according to the method of claim 1 or 2, wherein the new variety of four-leaflet clover has features in comparison to the wild-type three-leaflet clover Trifolium repens L., as disclosed in table 7 below:

TABLE 7

| Features | New variety of clover | Wild-type clover |
| --- | --- | --- |
| Height | 7~25 cm | 5~20 cm |
| Numbers of leaves | Four | Three |
| Shape of leaves | Heart | Ellipse |
| Surface of leaf | Fluffy | Fluffy |
| Periphery of leaf | A pattern of teeth of comb | A pattern of teeth of comb |
| Length of leaf | 0.3~2.5 cm | 0.7~3.0 cm |
| Width of leaf | 0.3~2.5 cm | 0.5~2.0 cm |
| Color of leaf | Light green | Dark green |
| Shape of stem | Separated from ground surface | Creeping on ground |
| Numbers of stems | 6~10 stems | Irregular |
| Shape of roots | Straight | Creeping or straight |
| Lifetime | Annual | Perennial |
| Flowering time | June | June |
| Shape of flower | Raceme having three receptacles | Raceme |
| Color of flower | White | White or pink |
| Heliophilous | Less heliophilous | heliophilous |
| Disease endurance | Strong | Strong |
| Cold resistance | Strong | Strong |
| Growth rate | Rapid | Rapid |
| ornamental value | Valuable (light green, four-leaflet) | Worthless (oval shape) |

\* \* \* \* \*